United States Patent
Cole

(10) Patent No.: US 7,220,756 B2
(45) Date of Patent: May 22, 2007

(54) N-SULFONYLHETEROCYCLOPYRROLYL-ALKYLAMINE COMPOUNDS AS 5-HYDROXYTRYPTAMINE-6 LIGANDS

(75) Inventor: Derek Cecil Cole, New City, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/344,765

(22) Filed: Feb. 1, 2006

(65) Prior Publication Data

US 2006/0160878 A1    Jul. 20, 2006

Related U.S. Application Data

(62) Division of application No. 10/909,092, filed on Jul. 30, 2004, now Pat. No. 7,041,695.

(60) Provisional application No. 60/491,622, filed on Jul. 31, 2003.

(51) Int. Cl.
   - *A61K 31/407* (2006.01)
   - *A61K 31/429* (2006.01)
   - *C07D 215/36* (2006.01)
   - *C07D 513/06* (2006.01)
   - *C07D 471/04* (2006.01)

(52) U.S. Cl. .............. 514/300; 514/314; 514/368; 514/414; 546/121; 546/172; 548/126; 548/453

(58) Field of Classification Search ........... 548/151, 548/304.4; 514/368
See application file for complete search history.

(56) References Cited

U.S. PATENT DOCUMENTS 6,528,653 B2   3/2003   Gill et al.
6,730,694 B1   5/2004   Beight et al.
7,041,695 B2 *  5/2006   Cole .................. 514/412

FOREIGN PATENT DOCUMENTS

WO   WO 2004/018479 A1   3/2004
WO   WO 2004/018480 A1   3/2004

OTHER PUBLICATIONS

Hegedus et al., "The Chemistry of N-Sulfonyl Enamines," J. Org. Chem. 1986, 51, 1171-1174.*
Riemer, et al., "Influence of the 5-HT6 Receptor on Acetylcholine Release in the Cortex: Pharmacological Characterization of 4-(2-Bromo-6-pyrrolidin-1-ylpyridine-4-sulfonyl)phenylamine, . . . ," J. Med. Chem. vol. 46, 1273-1276 (2003).*
David Wensbo et al., *Tetrahedron Letters*, 1995, vol. 51, No. 37, 10323-10342.
Joseph B. Blair et al., *Journal of Medicinal Chemistry*, 1999, vol. 42, No. 6, 1106-1111.

* cited by examiner

Primary Examiner—Kamal A. Saeed
Assistant Examiner—Andrew B. Freistein
(74) Attorney, Agent, or Firm—Barbara L. Lences

(57) ABSTRACT

The present invention provides a compound of formula I and the use thereof for the therapeutic treatment of a CNS disorder relating to or affected by the 5-HT6 receptor

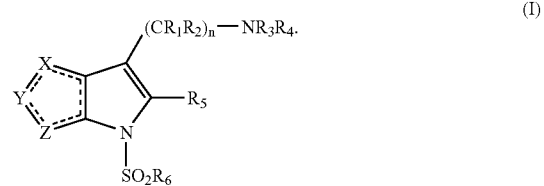

15 Claims, No Drawings

N-SULFONYLHETEROCYCLOPYRROLYL-ALKYLAMINE COMPOUNDS AS 5-HYDROXYTRYPTAMINE-6 LIGANDS

This is a divisional of application Ser. No. 10/909,092 filed on Jul. 30, 2004 which issued as U.S. Pat. No. 7,041,695, which claims the benefit of provisional application Ser. No. 60/491,622, filed Jul. 31, 2003, each application is hereby incorporated by reference in its entirety.

BACKGROUND OF THE INVENTION

Serotonin (5-Hydroxytryptamine)(5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320–327) and subsequently from human tissue (Kohen, R.; Metcalf, M. A.; Khan, N.; Druck, T.; Huebner, K.; Sibley, D. R. *Journal of Neurochemistry* 1996, 66, 47–56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268–276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105–1111).

There are many potential therapeutic uses for 5-HT6 ligands in humans based on direct effects and on indications from available scientific studies. These studies include the localization of the receptor, the affinity of ligands with known in vivo activity, and various animal studies conducted so far.

One potential therapeutic use of modulators of 5-HT6 receptor function is in the enhancement of cognition and memory in human diseases such as Alzheimer's.

The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; E I Mestikawy, S. *Brain Research*, 1997, 746, 207–219). The ability of known 5-HT6 receptor ligands to enhance cholinergic transmission also supports the potential cognition use (Bentley, J. C.; Boursson, A.; Boess, F. G.; Kone, F. C.; Marsden, C. A.; Petit, N.; Sleight, A. J. *British Journal of Pharmacology*, 1999, 126(7), 1537–1542). Studies have found that a known 5-HT6 selective antagonist significantly increased glutamate and aspartate levels in the frontal cortex without elevating levels of noradrenaline, dopamine, or 5-HT. This selective elevation of neurochemicals known to be involved in memory and cognition strongly suggests a role for 5-HT6 ligands in cognition (Dawson, L. A.; Nguyen, H. O.; Li, P. *British Journal of Pharmacology*, 2000, 130(1), 23–26). Animal studies of memory and learning with a known selective 5-HT6 antagonist found some positive effects (Rogers, D. C.; Hatcher, P. D.; Hagan, J. J. *Society of Neuroscience, Abstracts* 2000, 26, 680 and Foley, A. G. et al, Neuropsychopharmacology, 2004, 29(1), 93–100).

A related potential therapeutic use for 5-HT6 ligands is the treatment of attention deficit disorders (ADD, also known as Attention Deficit Hyperactivity Disorder or ADHD) in both children and adults. Because 5-HT6 antagonists appear to enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901–5907), 5-HT6 antagonists may attenuate attention deficit disorders.

Early studies examining the affinity of various CNS ligands with known therapeutic utility or a strong structural resemblance to known drugs suggests a role for 5-HT6 ligands in the treatment of schizophrenia and depression. For example, clozapine (an effective clinical antipsychotic) has high affinity for the 5-HT6 receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319–334).

Further, recent in vivo studies in rats indicate 5-HT6 modulators may be useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606–1612).

Taken together, the above studies strongly suggest that compounds which are 5-HT6 receptor ligands may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g., anxiety, depression and obsessive compulsive disorders; the treatment of motion or motor disorders such as Parkinson's disease and epilepsy; the treatment of diseases associated with neurodegeneration such as stroke and head trauma; or withdrawal from drug addiction including addiction to nicotine, alcohol, and other substances of abuse.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides an N-sulfonylheterocyclopyrrolylalkylamine derivative of formula I

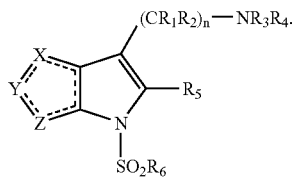

wherein
- X is $CR_7$, $SO_m$, O or $NR_8$;
- Y is $CR_9$, $SO_m$, O or $NR_8$;
- Z is $CR_{10}$, $SO_m$, O or $NR_8$ with the proviso that two of X, Y and Z must be $CR_7$, $CR_9$ or $CR_{10}$;
- $R_1$ and $R_2$ are each independently H, OH or an optionally substituted $C_1$–$C_6$alkyl group;
- $R_3$ and $R_4$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted or $R_3$ and $R_4$ may be taken together with the atom to which they are attached to form an optionally substituted 5- to 8-membered ring optionally containing an additional heteroatom selected from O, $NR_{11}$ or $SO_x$;
- $R_5$ is H, halogen, or a $C_1$–$C_6$alkyl, $C_2$–$C_6$alkoxy, $C_3$–$C_7$cycloalkyl, aryl or heteroaryl group each optionally substituted;
- $R_6$ is an optionally substituted $C_1$–$C_6$alkyl, $C_3$–$C_7$cycloalkyl, aryl or heteroaryl group or an optionally substituted 8- to 13-membered bicyclic or tricyclic ring system having a N atom at the bridgehead and optionally containing 1, 2 or 3 additional heteroatoms selected from N, O, or S;
- n is an integer of 2, 3, 4 or 5;
- $R_7$, $R_9$ and $R_{10}$ are each independently H, halogen, CN, $OCO_2R_{12}$, $CO_2R_{13}$, $CONR_{14}R_{15}$, $SO_pR_{16}$, $NR_{17}R_{18}$, $OR_{19}$, $COR_{20}$, or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;
- $R_8$, $R_{11}$, $R_{12}$, $R_{13}$, $R_{16}$, $R_{19}$, and $R_{20}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
- $R_{14}$ and $R_{15}$ are each independently H or an optionally substituted $C_1$–$C_6$alkyl group or $R_{14}$ and $R_{15}$ may be taken together with the atom to which they are attached to form a 5- to 7-membered ring optionally containing another heteroatom selected from O, $NR_{21}$ or S;
- $R_{17}$ and $R_{18}$ are each independently H or an optionally substituted $C_1$–$C_4$alkyl group or $R_{17}$ and $R_{18}$ may be taken together with the atom to which they are attached to form a 5- to 7-membered ring optionally containing another heteroatom selected from O, $NR_{22}$ or $SO_q$;
- $R_{21}$ and $R_{22}$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted; and
- m, p, q and x are each independently 0 or an integer of 1 or 2; and
- ------- represents a single bond or a double bond; or a stereoisomer thereof or a pharmaceutically acceptable salt thereof.

The present invention also provides methods and compositions useful for the therapeutic treatment of central nervous system disorders related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104–109, Pharma Press Ltd.

Surprisingly, it has now been found that N-sulfonylheterocyclo-pyrrolylalkylamine derivatives of formula I demonstrate 5-HT6 affinity. Advantageously, said alkylamine derivatives may be used as effective therapeutic agents for the treatment of central nervous system (CNS) disorders associated with or affected by the 5-HT6 receptor. Accordingly, the present invention provides N-sulfonylheterocyclo-pyrrolylalkylamine derivatives of formula I

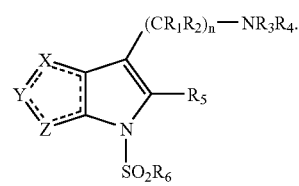

wherein
- X is $CR_7$, $SO_m$, O or $NR_8$;
- Y is $CR_9$, $SO_m$, O or $NR_8$;
- Z is $CR_{10}$, $SO_m$, O or $NR_8$ with the proviso that two of X, Y and Z must be $CR_7$, $CR_9$ or $CR_{10}$;
- $R_1$ and $R_2$ are each independently H, OH or an optionally substituted $C_1$–$C_6$alkyl group;
- $R_3$ and $R_4$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted or $R_3$ and $R_4$ may be taken together with the atom to which they are attached to form an optionally substituted 5- to 8-membered ring optionally containing an additional heteroatom selected from O, $NR_{11}$ or $SO_x$;
- $R_5$ is H, halogen, or a $C_1$–$C_6$alkyl, $C_2$–$C_6$alkoxy, $C_3$–$C_7$cycloalkyl, aryl or heteroaryl group each optionally substituted;
- $R_6$ is an optionally substituted $C_1$–$C_6$alkyl, $C_3$–$C_7$cycloalkyl, aryl or heteroaryl group or an optionally substituted 8- to 13-membered bicyclic or tricyclic ring system having a N atom at the bridgehead and optionally containing 1, 2 or 3 additional heteroatoms selected from N, O, or S;

n is an integer of 2, 3, 4 or 5;

$R_7$, $R_9$ and $R_{10}$ are each independently H, halogen, CN, $OCO_2R_{12}$, $CO_2R_{13}$, $CONR_{14}R_{15}$, $SO_pR_{16}$, $NR_{17}R_{18}$, $OR_{19}$, $COR_{20}$, or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;

$R_8$, $R_{11}$, $R_{12}$, $R_{13}$, $R_{16}$, $R_{19}$, and $R_{20}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{14}$ and $R_{15}$ are each independently H or an optionally substituted $C_1$–$C_6$alkyl group or $R_{14}$ and $R_{15}$ may be taken together with the atom to which they are attached to form a 5- to 7-membered ring optionally containing another heteroatom selected from O, $NR_{21}$ or S;

$R_{17}$ and $R_{18}$ are each independently H or an optionally substituted $C_1$–$C_4$alkyl group or $R_{17}$ and $R_{18}$ may be taken together with the atom to which they are attached to form a 5- to 7-membered ring optionally containing another heteroatom selected from O, $NR_{22}$ or $SO_q$;

$R_{21}$ and $R_{22}$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted; and m, p, q and x are each independently 0 or an integer of 1 or 2; and -------- represents a single bond or a double bond; or a stereoisomer thereof or a pharmaceutically acceptable salt thereof.

In the specification and claims, the group

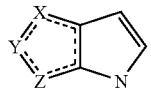

designates

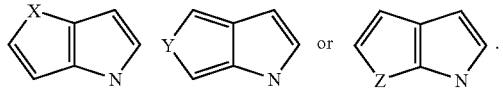

As used in the specification and claims, the term halogen designates F, Cl, Br or I and the term cycloheteroalkyl designates a 5- to 7-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein $X_1$ is NR, O or S; and R is H or an optional substituent as described hereinbelow:

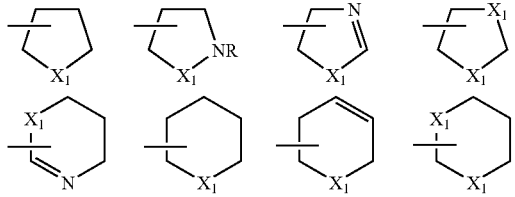

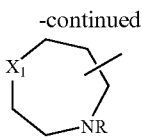

Similarly, as used in the specification and claims, the term heteroaryl designates a 5- to 10-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term aryl designates a carbocyclic aromatic ring system e.g., having 6 to 14 carbon atoms such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein W is NR, O or S; and R is H or an optional substituent as described hereinbelow:

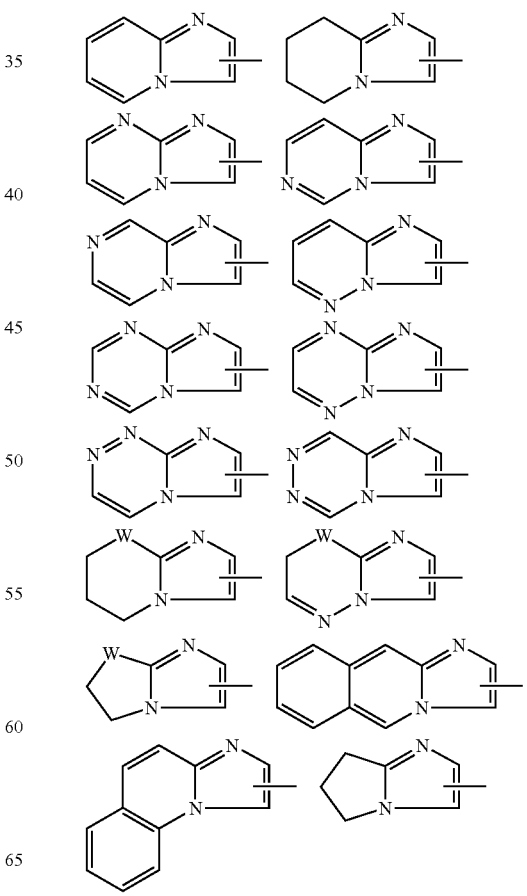

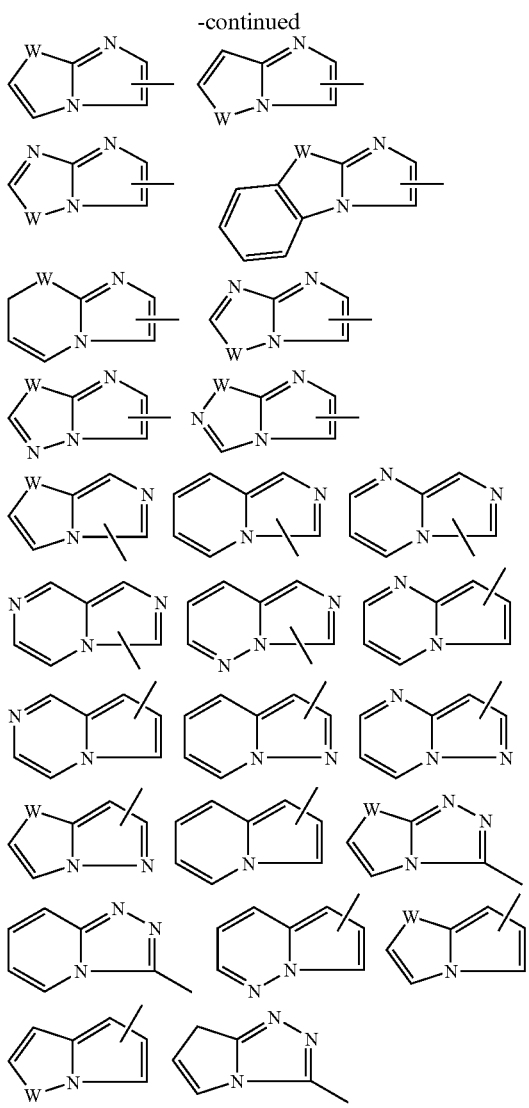

In the specification and claims, when the terms $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl as designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl (such as heteroaryl or cycloheteroalkyl) or cycloalkyl groups, preferably halogen atoms or lower (e.g. $C_1$–$C_6$) alkyl groups. Typically, 0–3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein X or Z is $SO_m$. Also preferred are those compounds of formula I wherein n is 2. Another group of preferred compounds of formula I are those compounds wherein $R_6$ is an optionally substituted aryl or heteroaryl group or an optionally substituted 8- to 13-membered bicyclic or tricyclic ring system having a N atom at the bridgehead and optionally containing 1, 2 or 3 additional heteroatoms selected from N, O or S.

More preferred compounds of the invention are those formula I compounds wherein Z is $SO_m$ and m is 0. Another group of more preferred compounds are those formula I compounds wherein n is 2 and $R_3$ and $R_4$ are each independently H or $CH_3$. Further more preferred compounds are those formula I compounds wherein Z is S; n is 2; $R_6$ is an optionally substituted phenyl, naphthyl, thienyl or imidazothiazolyl group; $R_1$, $R_2$ and $R_5$ are H; and $R_3$ and $R_4$ are each independently H or $C_1$–$C_3$alkyl.

Examples of preferred compounds of the invention include:

2-[6-(phenylsulfonyl)-6H-thieno[2,3-b]pyrrol-4-yl]ethylamine;

2-{[6-(3-trifluoromethyl)phenylsulfonyl]-6H-thieno[2,3-b]pyrrol-4-yl}ethylamine;

2-{[6-(3-Chlorophenyl)sulfonyl]-6H-thieno[2,3-b]pyrrol-4-yl}ethylamine;

2-{[6-(5-Chlorothien-2-yl)sulfonyl]-6H-thieno[2,3-b]pyrrol-4-yl}ethylamine;

2-{[6-(6-Chloroimidazo[2,1-b][1,3]thiazol-5-yl)sulfonyl]-6H-thieno[2,3-b]pyrrol-4-yl}-ethylamine;

2-[6-(2-naphthylsulfonyl)-6H-thieno[2,3-b]pyrrol-4-yl]ethylamine;

2-{[6-(3-methoxyphenyl)sulfonyl]-6H-thieno[2,3-b]pyrrol-4-yl}ethylamine;

2-{[6-(5-chloro-3-methylbenzo[b]thien-2-yl)sulfonyl]-6H-thieno[2,3-b]pyrrol-4-yl}-ethylamine;

2-{[6-(2-fluorophenyl)sulfonyl]-6H-thieno[2,3-b]pyrrol-4-yl}ethylamine;
2-{[6-(3-fluorophenyl)sulfonyl]-6H-thieno[2,3-b]pyrrol-4-yl}ethylamine;
2-{[6-(2-chlorophenyl)sulfonyl]-6H-thieno[2,3-b]pyrrol-4-yl}ethylamine;
2-{[6-(imidazo[2,1-b][1,3]thiazol-5-yl)sulfonyl]-6H-thieno[2,3-b]pyrrol-4}ethylamine;
2-{[6-(2-chloroimidazo[1,2-a]pyrid-3-yl)sulfonyl]-6H-thieno[2,3-b]pyrrol-4-yl]-ethylamine;
2-{[6-(2,6-dichloroimidazo[2,1-b][1,3]thiazol-5-yl)sulfonyl]-6H-thieno[2,3-b]pyrrol-4-yl]-ethylamine;
2-{[6-(4-chlorophenyl)sulfonyl]-6H-thieno[2,3-b]pyrrol-4-yl}ethylamine;
2-{[6-(2,3-dichlorophenyl)sulfonyl)-6H-thieno[2,3-b]pyrrol-4-yl}ethylamine;
2-{[6-(3-bromophenyl)sulfonyl]-6H-thieno[2,3-b]pyrrol-4-yl}ethylamine; 2-{[6-(5-bromothien-2-yl)sulfonyl]-6H-thieno[2,3-b]pyrrol-4-yl}ethylamine;
2-[6-(thien-2-ylsulfonyl)-6H-thieno[2,3-b]pyrrol-4-yl-ethylamine;
2-{[6-(4,5-dichlorothien-2-yl)sulfonyl]-6H-thieno[2,3-b]pyrrol-4-yl}ethylamine;
2-[6-(1-naphthylsulfonyl)-6H-thieno[2,3-b]pyrrol-4-yl]ethylamine;
2-{[6-(3-methylphenyl)sulfonyl]-6H-thieno[2,3-b]pyrrol-4-yl}ethylamine;
2-{[6-(1,2-dimethyl-1H-imidazol-4-yl)sulfonyl]-6H-thieno[2,3-b]pyrrol-4-yl}ethylamine;
2-{[6-(quinolin-8-yl)sulfonyl]-6H-thieno[2,3-b]pyrrol-4-yl]-ethylamine;
2-{{[6-(2-trifluoromethyl)phenyl]sulfonyl}-6H-thieno[2,3-b]pyrrol-4-yl}ethylamine;
2-{[6-(4-methoxyphenyl)sulfonyl]-6H-thieno[2,3-b]pyrrol-4-yl}ethylamine;
2-{[6-(3-chloro-2-methylphenyl)sulfonyl]-6H-thieno[2,3-b]pyrrol-4-yl}ethylamine;
2-{[6-(4-aminophenyl)sulfonyl]-6H-thieno[2,3-b]pyrrol-4-yl}ethylamine;
N,N-dimethyl-2-[(6-phenylsulfonyl)-6H-thieno[2,3-b]pyrrol-4-yl]ethylamine;
N,N-dimethyl-2-{{[6-(3-trifluoromethylphenyl]sulfonyl}-6H-thieno[2,3-b]pyrrol-4-yl}-ethylamine;
N,N-dimethyl-2-{[6-(3-chlorophenyl)sulfonyl]-6H-thieno[2,3-b]pyrrol-4-yl}ethylamine;
N,N-dimethyl-2-{[6-(5-chlorothien-2-yl)sulfonyl]-6H-thieno[2,3-b]pyrrol-4-yl]-ethyl}-amine;
N,N-dimethyl-2-{[6-(6-chloroimidazo[2,1-b][1,3]thiazol-5-yl)sulfonyl]-6H-thieno[2,3-b]pyrrol-4-yl}ethylamine;
N,N-dimethyl-2-[6-(2-naphthylsufonyl)-6H-thieno[2,3-b]pyrrol-4-yl]ethylamine;
N,N-dimethyl-2-{[6-(3-methoxyphenyl)sulfonyl]-6H-thieno[2,3-b]pyrrol-4-yl]-ethyl}-amine;
N,N-dimethyl-2-{[6-(5-chloro-3-methylbenzo[b]thien-2-yl)sulfonyl]-6H-thieno[2,3-b]pyrrol-4-yl}ethylamine;
N,N-dimethyl-2-{[6-(2-fluorophenyl)sulfonyl]-6H-thieno[2,3-b]pyrrol-4-yl}ethylamine;
N,N-dimethyl-2-{[6-(3-fluorophenyl)sulfonyl]-6H-thieno[2,3-b]pyrrol-4-yl]-ethylamine;
N,N-dimethyl-2-{[6-(2-chlorophenyl)sulfonyl]-6H-thieno[2,3-b]pyrrol-4-yl}ethylamine;
N,N-dimethyl-2-{[6-(imidazo[2,1-b][1,3]thiazol-5-yl)sulfonyl]-6H-thieno[2,3-b]pyrrol-4-yl}-ethylamine;
N,N-dimethyl-2-{[6-(2-chloroimidazo[1,2-a]pyridin-3-yl)sulfonyl]-6H-thieno[2,3-b]pyrrol-4-yl}ethylamine;
N,N-dimethyl-2-{[6-(2,6-dichloroimidazo[2,1-b]thiazol-5-yl)sulfonyl]-6H-thieno[2,3-b]pyrrol-4-yl}ethylamine;
N,N-dimethyl-2-{[6-(4-chlorophenyl)sulfonyl]-6H-thieno[2,3-b]pyrrol-4-yl}ethylamine;
N,N-dimethyl-2-{[6-(2,3-dichlorophenyl)sulfonyl]-6H-thieno[2,3-b]pyrrol-4-yl}ethyl-amine;
N,N-dimethyl-2-{[6-(3-bromophenyl)sulfonyl]-6H-thieno[2,3-b]pyrrol-4-yl]-ethylamine;
N,N-dimethyl-2-{[6-(5-bromothien-2-yl)sulfonyl]-6H-thieno[2,3-b]pyrrol-4-ylethyl]-amine;
N,N-dimethyl-2-{(6-thien-2-ylsulfonyl)-6H-thieno[2,3-b]pyrrol-4-yl]-ethyllamine;
N,N-dimethyl-2-{[6-(4,5-dichlorothien-2-yl)sulfonyl]-6H-thieno[2,3-b]pyrrol-4-yl]-ethyl-amine;
N,N-dimethyl-2-{[6-(1-naphthyl)sulfonyl]-6H-thieno[2,3-b]pyrrol-4-yl}ethylamine;
N,N-dimethyl-2-{[6-(3-methylphenyl)sulfonyl]-6H-thieno[2,3-b]pyrrol-4-yl}ethylamine;
N,N-dimethyl-2-{[6-(1,2-dimethyl-1H-imidazol-4-yl)sulfonyl]-6H-thieno[2,3-b]pyrrol-4-yl}ethylamine;
N,N-dimethyl-2-{[6-(8-quinolinyl)sulfonyl]-6H-thieno[2,3-b]pyrrol-4-yl}ethylamine;
N,N-dimethyl-2-{{[6-(2-trifluoromethyl)phenyl]sulfonyl}-6H-thieno[2,3-b]pyrrol-4-yl}ethylamine;
N,N-dimethyl-2-{[6-(4-methoxyphenyl)sulfonyl]-6H-thieno[2,3-b]pyrrol-4-yl}ethyl-amine;
N,N-dimethyl-2-{[6-(3-chloro-2-methylphenyl)sulfonyl]-6H-thieno[2,3-b]pyrrol-4-yl]-ethylamine;
2-{[4-(3-chlorophenyl)sulfonyl]-4H-thieno[3,2-b]pyrrol-6-yl}ethylamine;
2-{[4-(2-naphthyl)sulfonyl]-4H-thieno[2,3-b]pyrrol-6-yl}ethylamine;
2-{[4-(3-methoxyphenyl)sulfonyl]-4H-thieno[3,2-b]pyrrol-6-yl}ethylamine;
2-{[4-(5-chloro-3-methyl-benzo[b]thien-2-yl)sulfonyl]-4H-thieno[2,3-b]pyrrol-6-yl]-ethylamine;
2-{[4-(2-chlorophenyl)sulfonyl]-4H-thieno[3,2-b]pyrrol-6-yl}ethylamine;
N,N-dimethyl-2-[4-(phenylsulfonyl)-4H-thieno[2,3-b]pyrrol-6-yl]ethyl]amine;
N,N-dimethyl-2-{[4-(3-trifluoromethylphenyl)sulfonyl]-4H-thieno[2,3-b]pyrrol-6-yl}-ethylamine;
N,N-dimethyl-2-{[4-(3-chlorophenyl)sulfonyl]-4H-thieno[2,3-b]pyrrol-6-yl}ethylamine;
N,N-dimethyl-2-{[4-(5-chlorothien-2-yl)sulfonyl]-4H-thieno[2,3-b]pyrrol-6-yl}ethyl-amine;
N,N-dimethyl-2-{[4-(4-chloroimidazo[2,1-b][1,3]thiazol-5-yl)sulfonyl]-4H-thieno[2,3-b]-pyrrol-6-yl}ethylamine;
N,N-dimethyl-2-{[4-(2-naphthyl)sulfonyl]-4H-thieno[2,3-b]pyrrol-6-yl}-ethylamine;
N,N-dimethyl-2-{[4-(3-methoxyphenyl)sulfonyl]-4H-thieno[2,3-b]pyrrol-6-yl}ethyl-amine;
N,N-dimethyl-2-{[4-(5-chloro-3-methyl-benzo[b]thien-2-yl)sulfonyl]-4H-thieno[2,3-b]pyrrol-6-yl}ethylamine;
N,N-dimethyl-2-{[4-(2-fluorophenyl)sulfonyl]-4H-thieno[2,3-b]pyrrol-6-yl}ethylamine;
N,N-dimethyl-2-{[4-(3-fluorophenyl)sulfonyl]-4H-thieno[2,3-b]pyrrol-6-yl}ethylamine;
N,N-dimethyl-2-{[4-(2-chlorophenyl)sulfonyl]-4H-thieno[2,3-b]pyrrol-6-yl}ethylamine;
N,N-dimethyl-2-{[4-(imidazo[2,1-b][1,3]thiazol-5-yl)sulfonyl]-4H-thieno[2,3-b]pyrrol-6-yl}ethylamine;
N,N-dimethyl-2-[(4-phenylsulfonyl)-4H-furo[3,2-b]pyrrol-6-yl]ethylamine;
N,N-dimethyl-2-{[4-(6-chloroimidazo[2,1-b][1,3]thiazol-5-yl)sulfonyl]-4H-furo[3,2-b]-pyrrol-6-yl}ethylamine;
2-[1-(phenylsulfonyl)-4-methyl-1,4-dihydro-pyrrolo[3,2-b]pyrrol-3-yl}ethylamine;

N,N-dimethyl-2-{[1-(6-chloroimidazo[2,1-b]thiazol-5-yl)
sulfonyl]-4-methyl-1,4-dihydro-pyrrolo[3,2-b]pyrrol-3-
yl}ethylamine;
2-[(1-phenylsulfonyl)-1H-thieno[3,4-b]pyrrol-3-yl]ethy-
lamine;
2-{[1-(6-chloroimidazo[2,1-b]thiazol-5-yl)sulfonyl]-1H-
thieno[3,4-b]pyrrol-3-yl}-ethylamine;
N,N-dimethyl-2-[(1-phenylsulfonyl)-1H-thieno[3,4-b]pyr-
rol-3-yl]ethylamine;
N,N-dimethyl-2-{[1-(6-chloroimidazo[2,1-b]thiazol-5-yl)
sulfonyl]-1H-thieno[3,4-b]-pyrrol-3-yl}ethylamine;
N,N-dimethyl-2-[(1-phenylsulfonyl)-1H-furo[3,4-b]pyrrol-
3-yl]ethylamine;
N,N-dimethyl-2-{[1-(6-chloroimidazo[2,1-b][1,3]thiazol-5-
yl)sulfonyl]-1H-furo[3,4-b]-pyrrol-3-yl}ethylamine;
2-[(1-phenylsulfonyl)-5-methyl-1,5-dihydro-pyrrolo[3,4-b]
pyrrol-3-yl]ethylamine;
N,N-dimethyl-2-{[1-(6-chloroimidazo[2,1-b][1,3]thiazol-5-
yl)sulfonyl]-5-methyl-1,5-dihydro-pyrrolo[3,4-b]pyrrol-
3-yl}ethylamine;
N,N-dimethyl-2-[(6-phenylsulfonyl)-6H-furo[2,3-b]pyrrol-
4-yl]ethylamine;
2-{[6-(6-chloroimidazo[2,1-b][1,3]thiazol-5-yl)sulfonyl]-
6H-furo[2,3-b]pyrrol-4-yl}-ethylamine;
2-[(1-phenylsulfonyl)-6-methyl-1,6-dihydro-pyrrolo[2,3-b]
pyrrol-3-yl]ethylamine;
N,N-dimethyl-2-{[1-(6-chloroimidazo[2,1-b][1,3]thiazol-5-
yl)sulfonyl]-6-methyl-1,6-dihydro-pyrrolo[2,3-b]pyrrol-
3-yl}ethylamine;
a steroisomer thereof; and
a pharmaceutically acceptable salt thereof.

Advantageously, the present invention provides a process for the preparation of a compound of formula I which comprises reacting a compound of formula II with a sulfonylchloride, $ClSO_2R_6$, in the presence of a base optionally in the presence of a solvent. The process of the invention is shown in flow diagram I.

Flow Diamgram I

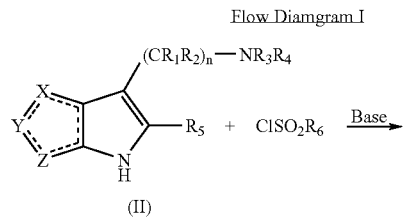

(II)

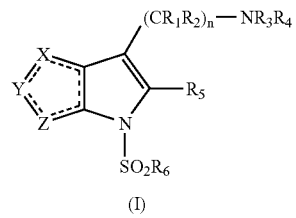

(I)

Bases suitable for use in the process of the invention include strong bases such as NaH, KOt-Bu, NaOH or any conventional base capable of removing a proton from a basic nitrogen atom.

Solvents suitable for use in the process of the invention include polar solvents such as dimethyl formamide, dimethyl sulfoxide, lower alkyl alcohol, acetonitrile, tetrahydrofuran, or the like.

Compounds of formula II may be prepared using conventional synthetic methods and, if required, standard separation or isolation techniques. For example, compounds of formula II wherein Z is S, O or $NR_8$; n is 2; and $R_1$, $R_2$ and $R_5$ are H (IIa) may be prepared in a manner similar to that described by Blair, J. B. et al, Journal Medicinal Chemistry (1999), 42, 1106–1111, i.e. by reacting a 3-iodo-2-carboxylic acid of formula III with diphenoxylphosphoryl azide and triethylamine in t-butanol to give the corresponding 3-iodo-2-(N-t-butoxycarbonyl)amine compound of formula IV; reacting said formula IV amine with ethyl 4-bromocrotonate in the presence of a base such as cesium carbonate to give the compound of formula V; cyclizing the formula V compound with palladium acetate [$Pd(OAc)_2$] and triphenylphosphine [$P(Ph)_3$] at an elevated temperature to give the protected heterocyclopyrrolo ester of formula VI; deprotecting the formula VI compound and reacting the deprotected ester with a methyl chloroaluminum amide of formula VII to give the heterocyclopyrrolo amide of formula VIII; and reducing said formula VIII amide with lithium aluminum hydride to give the desired formula IIa compound. The reaction is shown in flow diagram II wherein Boc represents t-butoxycarbonyl.

Flow Diamgram II

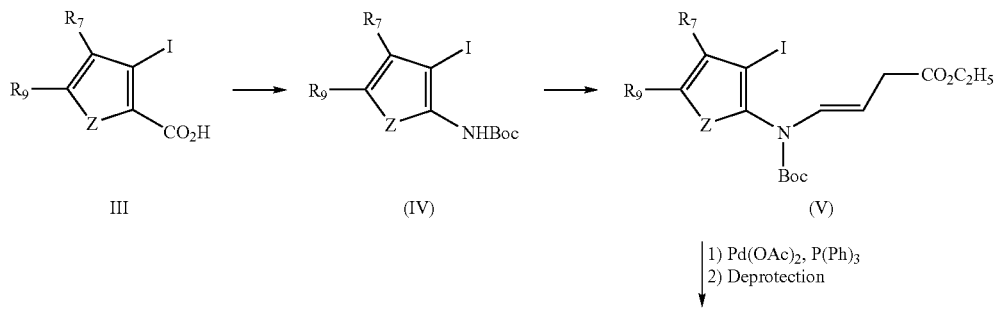

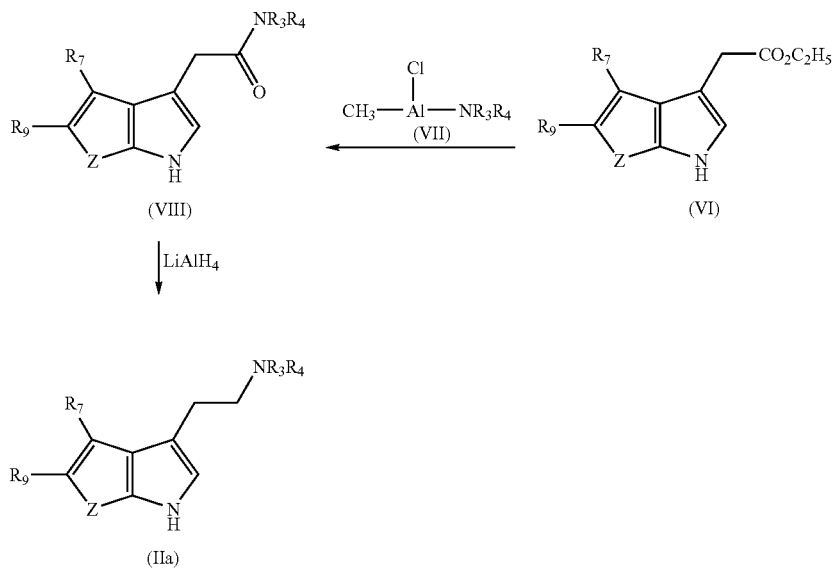

Similarly, compounds of formula II wherein X is S, O or $NR_8$; n is 2; and $R_1$, $R_2$ and $R_5$ are H (IIb) may be prepared by reacting a 3-carboxylic acid of formula IX with diphenylphosphonyl azide and triethylamine in t-butanol to give the corresponding 3-(protected)amine of formula X; reacting said formula X compound with N-iodosuccinimide in $CCl_4$ to give the 2-iodo-3-(protected)amine compound of formula XI; and treating the formula XI compound as shown in flow diagram II, i.e. alkylating with ethyl 4-bromocrotonate, cyclizing, deprotecting, reacting with a formula VII methyl choroaluminum amide and reducing with $LiAlH_4$ gives the desired compound of formula IIb. The reactions are shown in flow diagram III.

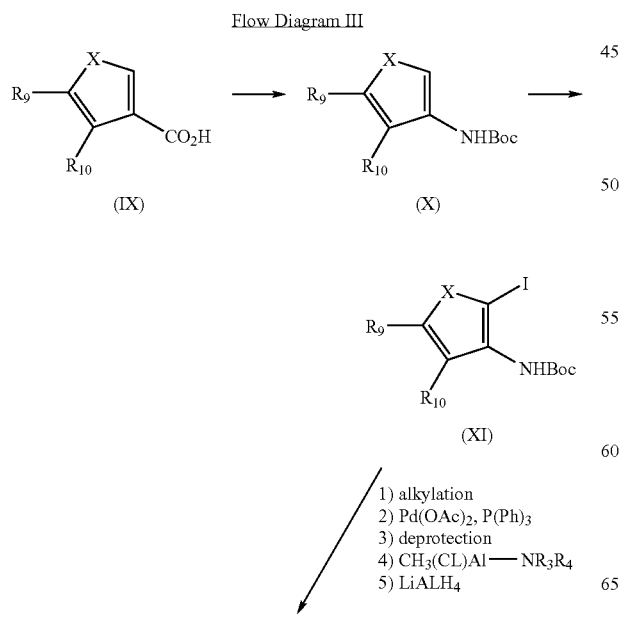

Compounds of formula II wherein Y is S, O or $NR_8$; n is 2; and $R_1$, $R_2$ and $R_5$ are H (IIc) may be prepared using essentially the same procedures described hereinabove in flow diagram I and employing a 4-iodo-3-carboxylic acid compound of formula XII as starting material. The reaction is shown in flow diagram IV.

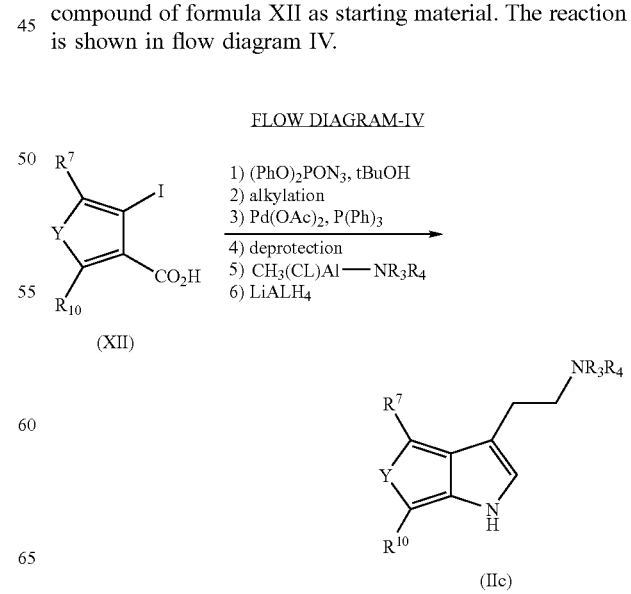

Compounds of formula XII may be prepared by standard procedures such as reacting 3,4-diiodothiophene, -furan or -pyrrole with lithium, followed by carbonylation; or by lithiation of a thiophene-, furan- or pyrrole-3-carboxylic acid followed by iodination, for example see Ayres, B. E. et al, Tetrahedron (1975), 31, 1755–1760.

Compounds of formula II wherein X, Y or Z is SO or $SO_2$ may be prepared by oxidizing a formula IIa, IIb or IIc compound with one or more equivalents of an oxidizing agent such as m-chloroperbenzoic acid.

Advantageously, the formula I compounds of the invention are useful for the treatment of CNS disorders relating to or affected by 5-HT6 receptor including motor, mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

The term HPLC designates high performance liquid chromatography. The terms EtOAc and DMF designate ethyl acetate and dimethyl formamide, respectively. The terms DMSO and THF designate dimethylsulfoxide and tetrahydrofuran, respectively. All chromatography is performed using $SiO_2$ as support.

EXAMPLE 1

Preparation of 2-(3-Iodothien-2-yl)carboxylic acid

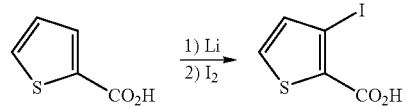

A solution of 2-thiophenecarboxylic acid (12.8 g, 0.1 mol) in THF at −78° C. is treated dropwise with n-butyl lithium (88 mL of 2.5 M solution in THF, 2.2 equiv), stirred for 0.5 h, treated dropwise with a solution of iodine (28 g) in THF (1.1 equiv.), allowed to warm to room temperature while stirring, and concentrated in vacuo. The resultant residue is dissolved in EtOAc and extracted with 10% aqueous $Na_2CO_3$. The aqueous extracts are combined, acidified with conc. HCl and extracted with EtOAc. The EtOAc extracts are combined, dried over $MgSO_4$ and concentrated in vacuo to afford the title product as a yellow-orange solid, 23.5 g (95% yield), identified by HPLC and mass spectral analyses.

EXAMPLE 2

Preparation of 3-Iodo-2-[(N-t-butoxycarbonyl)amino]thiophene

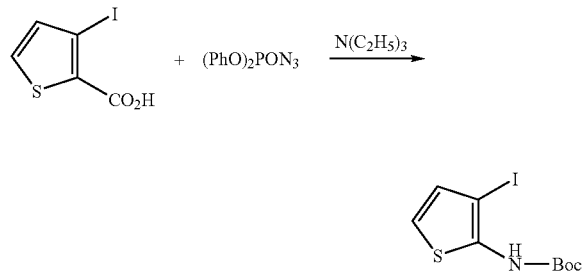

A mixture of 2-(3-iodothien-2-yl)carboxylic acid (23.5 g, 0.10 mol), triethylamine (15 mL, 1.1 equiv.) and diphenoxylphosphoryl azide [(PhO)$_2$PON$_3$] (30 g, 1.1 equiv.) in t-butanol is heated at reflux temperature for 16 h, cooled to room temperature, washed with saturated Na$_2$CO$_3$ and extracted with EtOAc. The extracts are combined, dried over MgSO$_4$ and concentrated in vacuo. The resultant residue is chromatographed (10% EtOAc in hexanes as eluent) to afford the title product as a brown solid, 10.5 g (35% yield), identified by HPLC and mass spectral analyses.

EXAMPLE 3

Preparation of Ethyl 1-[6-(t-butoxycarbonyl)-4-thieno[2,3-b]pyrrol-4-yl]acetate

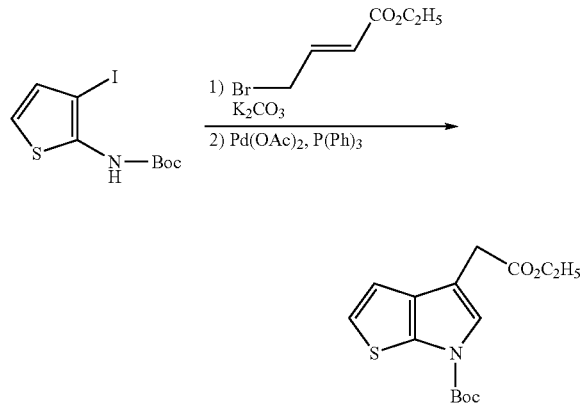

A mixture of 3-iodo-2-[(N-t-butoxycarbonyl)amino] thiophene (10 g, 32 mmol), K$_2$CO$_3$ (9 g, 2 equiv.) and ethyl 4-bromocrotonate (9 g, 1.5 equiv.) in DMF is stirred at room temperature for 16 h, treated with triphenylphosphine (838 mg, 0.1 equiv.) and palladium acetate (358 mg, 0.05 equiv.), heated at 70° C. for 8 h, cooled to room temperature, diluted with water and extracted with EtOAc. The extracts are combined, dried over MgSO$_4$ and concentrated in vacuo. The resultant residue is chromatographed (20% EtOAc in hexanes as eluent) to afford the title product as a clear oil, 8.6 g (90% yield), identified by HPLC and mass spectral analyses.

EXAMPLE 4

Preparation of Ethyl 1-(Thieno[2,3-b]pyrrol-4-yl)acetate

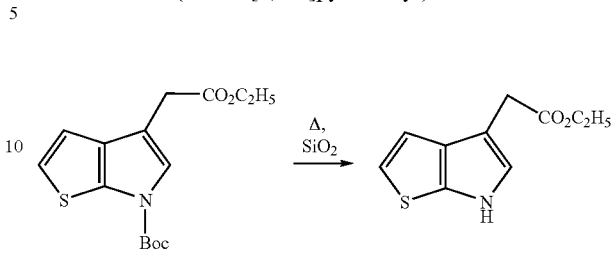

A solution of ethyl 1-[6-(t-butoxycarbonyl)-4-thieno[2,3-b]pyrrol-4-yl]acetate (8.6 g, 27 mmol) in CH$_2$Cl$_2$ is absorbed onto silica gel, concentrated in vacuo to remove the solvent and heated at 60° C. in vacuo for 48 h. The resultant dry silica gel mixture is placed on top of a silica gel column and eluted with 20% EtOAc in hexanes to afford the title product as clear oil, 2.48 g (42% yield), identified by liquid chromatography and mass spectral analyses.

EXAMPLE 5

Preparation of 1-(Thieno[2,3-b]pyrrol-4-yl)acetamide

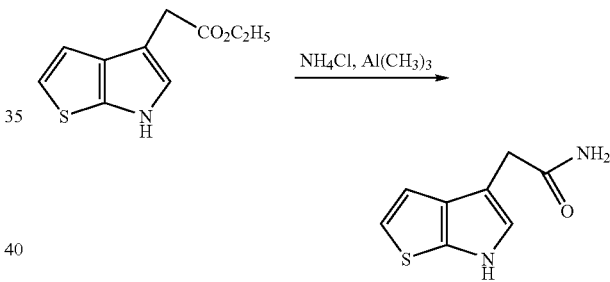

A stirred suspension of ammonium chloride (963 mg, 3 equiv.) in toluene at 5° C. is treated with trimethylaluminum (9 mL of 2 M solution in toluene, 3 equiv.), stirred at room temperature for 2 h, treated with a solution of ethyl 1-(thieno [2,3-b]pyrrol-4-yl)acetate (1.25 g, 6 mmol, 1 equiv.) in toluene, heated at 50° C. for 16 h, cooled to room temperature, quenched with water and extracted with EtOAc. The extracts are combined, dried over MgSO$_4$ and concentrated in vacuo to give the title product as a tan oil, 1.1 g (quantitative yield), identified by liquid chromatography and mass spectral analyses.

EXAMPLE 6

Preparation of 2-(6H-Thieno[2,3-b]pyrrol-4-yl)ethylamine

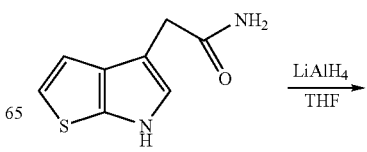

-continued

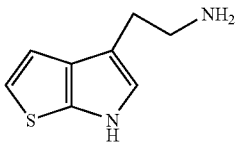

A stirred solution of 1-(thieno[2,3-b]pyrrol-4-yl)acetamide (1.08 g, 6 mmol) in THF is treated dropwise with a 1M solution of LiAlH$_4$ in THF (18 mL, 3 equiv.) stirred at 40° C. for 2 h, cooled-to room temperature, quenched with aqueous NaOH and extracted with EtOAc. The extracts are combined, dried over MgSO$_4$ and concentrated in vacuo to afford the title product as a tan oil, 1.0 g (quantitative yield), identified by HPLC and mass spectral analyses.

EXAMPLE 7

Preparation of N-(t-Butoxycarbonyl)-2-(6H-thieno[2,3-b]pyrrol-4-yl)ethylamine

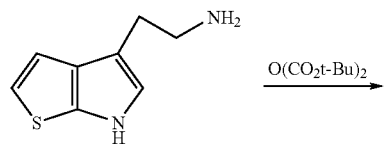

A stirred solution of 2-(6H-thieno[2,3-b]pyrrol-4-yl)ethylamine (1 g, 6 mmol) in 1:1 acetone/water is treated with K$_2$CO$_3$ (2.48 g, 3 equiv.) and di-t-butyldicarbonate (1.44 g, 1.1 equiv.), stirred at room temperature for 8 h, concentrated to remove the acetone and extracted with EtOAc. The extracts are combined, dried over MgSO$_4$ and EtOAc concentrated in vacuo to give the title product as a brown oil, 0.93 g (58% yield), identified by HPLC and mass spectral analyses.

EXAMPLE 8

Preparation of N-(t-Butoxycarbonyl)-2-[6-(phenylsulfonyl)thieno[2,3-b]pyrrol-4-yl]ethylamine -continued

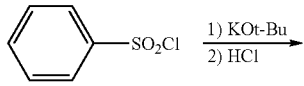

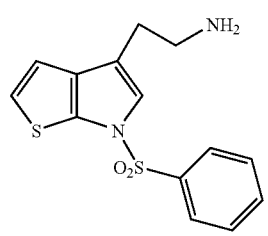

A mixture of N-(t-butoxycarbonyl)-2-(6H-thieno[2,3-b]pyrrol-4-yl)ethylamine (54 mg, 0.2 mmol), phenylsulfonyl chloride (70 mg, 0.22 mmol) and KOt-Bu (0.22 mL 1 M solution in THF, 0.22 mmol) in THF is shaken at ambient temperatures for 8 h and concentrated in vacuo. The resultant residue is dissolved in THF, treated with 4N HCl in dioxane (2 mL) shaken at room temperature for 16 h and concentrated in vacuo. This residue is dissolved in a mixture of DMSO, methanol and water and purified by preparative HPLC[1], to afford the title product, [M+H]307, retention time (RT) 1.53 min.

[1] Gilson Preparative HPLC conditions: Gilson Preparative HPLC system; YMC Pro-C18, 20 mm×50 mm ID, 5 uM column; 2 mL injection; Solvent A: 0.02% TFA/water; Solvent B:0.02% TFA/acetonitrile; Gradient: Time 0: 95% A; 2 min: 95% A; 14 min: 10% A, 15 min: 10% A, 16 min: 95% A; Flow rate 22.5 mL/min; Detection: 254 nm DAD.

EXAMPLES 9–35

Preparation of 2-[6-(Arylsulfonyl)6H-thieno[2,3-b]pyrrol-4-yl]ethylamine Derivatives Using essentially the same procedures described in example 8, hereinabove and employing the appropriate arylsulfonyl chloride, the compounds shown on Table I are obtained and identified by HPLC[2] and mass spectral analyses.

[2] HPLC Conditions: HP 1100 HPLC system; Waters Xterra MS C18, 2 mm (i.d.)×50 mm (length), 3.5 μm column, set at 50° C.; Flow rate 1.0 mL/min; Solvent A: 0.02% formic acid in water; Solvent B 0.02% formic acid in ACN; Gradient: Time O: 10% B; 2.5 min 90% B; 3 min 90% B; Sample concentration: ~2.0 mM; Injection volume: 5 uL; Detection: 220 nm, 254 nm DAD.

TABLE I

[Structure: thieno[2,3-b]pyrrole with CH2CH2NH2 at 4-position and SO2R6 on N]

| Ex. No. | R6 | [M + H] | RT (min) |
|---|---|---|---|
| 9 | 3-trifluorophenyl | 375 | 175 |
| 10 | 3-chlorophenyl | 342 | 1.64 |
| 11 | 5-chloro-thiophen-2-yl | 348 | 1.65 |
| 12 | 6-chloro-imidazo[2,1-b]thiazol-5-yl | 388 | 1.46 |
| 13 | 2-naphthyl | 357 | 1.76 |
| 14 | 3-methoxyphenyl | 337 | 1.57 |
| 15 | 5-chloro-3-methyl-benzo[b]thiophen-2-yl | 412 | 1.97 |
| 16 | 2-fluorophenyl | 325 | 1.43 |
| 17 | 3-fluorophenyl | 325 | 1.51 |
| 18 | 2-chlorophenyl | 342 | 1.52 |
| 19 | imidazo[2,1-b]thiazol-5-yl | 353 | 0.93 |
| 20 | 2-Chloro-imidazo[1,2-a]pyridine-3-yl | 382 | 1.48 |
| 21 | 2,6-dichloro-imidazo[2,1-b]thiazol-5-yl | 422 | 1.69 |
| 22 | 4-chlorophenyl | 342 | 1.65 |
| 23 | 2,3-dichlorophenyl | 376 | 1.72 |
| 24 | 3-bromophenyl | 386 | 1.69 |
| 25 | 5-bromo-thiophen-2-yl | 392 | 1.7 |
| 26 | 2-thiophene | 313 | 1.35 |
| 27 | 2,3-dichlorothiophen-5-yl | 382 | 1.83 |
| 28 | 1-naphthylene | 357 | 1.75 |
| 29 | 3-methylphenyl | 321 | 1.59 |
| 30 | 1,2-dimethyl-1H-imidazole-4-yl | 325 | 0.36 |
| 31 | 8-quinoline | 358 | 1.51 |
| 32 | 2-trifluoromethylphenyl | 375 | 1.69 |
| 33 | 4-methoxyphenyl | 337 | 1.58 |
| 34 | 3-chloro-2-methylphenyl | 356 | 1.78 |
| 35 | 4-aminophenyl | 322 | 1.09 |

EXAMPLE 36

Preparation of N,N-Dimethyl-2-(6H-thieno[2,3-b]pyrrol-4-yl)acetamide

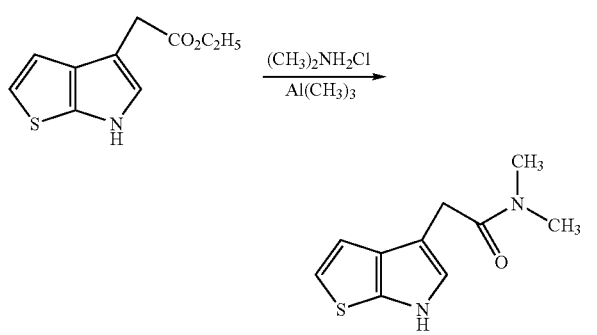

A stirred suspension of dimethylammonium chloride (978 mg, 2 equiv.) in toluene at 5° C. is treated with trimethyl aluminum (6 mL 2M solution in toluene, 2 equiv.), stirred at room temperature for 2 h, treated with ethyl 1-(thieno[2,3-b]pyrrol-4-yl)acetate (1.25 g, 6 mmol, 1 equiv.), heated at 80° C. for 2 h, cooled to room temperature, quenched with water and extracted with EtOAc. The extracts are combined, dried over MgSO4 and concentrated in vacuo to afford the title product, identified by liquid chromatography and mass spectral analyses.

EXAMPLE 37

Preparation of N,N-Dimethyl-2-(6H-thieno[2,3-b]pyrrol-4-yl)ethylamine

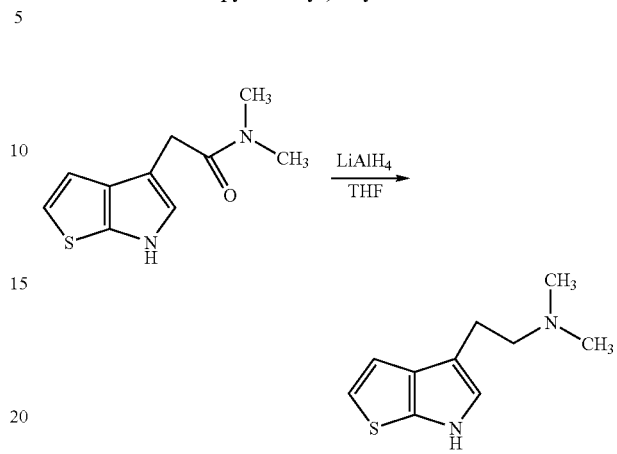

A stirred N,N-dimethyl-2-(6H-thieno[2,3-b]pyrrol-4-yl]acetamide (1.16 g, 6 mmol) in THF is treated with LiALH4 (18 mL of 1M solution in THF, 3 equiv.) at room temperature, stirred at 40° C. for 2 h, cooled to room temperature, quenched with aqueous NaOH and extracted with EtOAc. The extracts are combined, dried over MgSO4 and concentrated in vacuo to afford the title product as a tan oil, 0.81 g (89% yield), identified by HPLC and mass spectral analyses.

EXAMPLE 38

Preparation of N,N-Dimethyl-2-[6-(phenylsulfonyl)-6H-thieno[2,3-b]pyrrol-4-yl]ethylamine

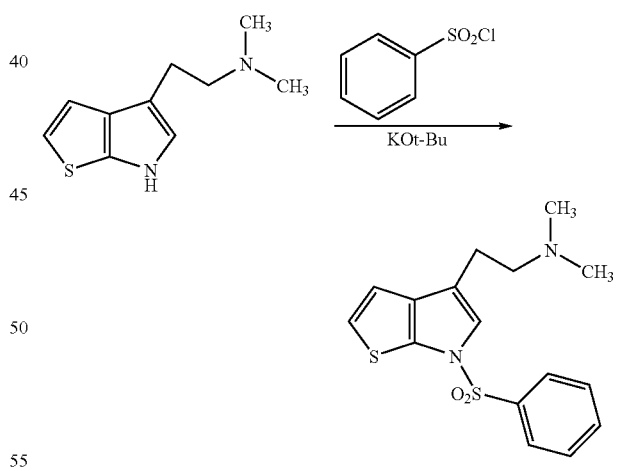

A mixture of N,N-dimethyl-2-(6H-thieno[2,3-b]pyrrol-4-yl)ethylamine (0.2 mmol), benzenesulfonyl chloride (0.22 mmol) and KOt-Bu (0.22 mmol) in THF is shaken at ambient temperatures for 8 h and concentrated in vacuo. The resultant residue is dissolved in a mixture of DMSO, methanol and water and purified by preparative HPLC[1] to afford the title product, [M+H] 335, retention time (RT) 1.42 min.

[1] Gilson Preparative HPLC conditions: Gilson Preparative HPLC system; YMC Pro C18, 20 mm×50 mm ID, 5 uM column; 2 mL injection; Solvent A: 0.02% TFA/water; Solvent B:0.02% TFA/acetonitrile; Gradient: Time 0: 95% A; 2 min: 95% A; 14 min: 10% A, 15 min: 10% A, 16 min: 95% A; Flow rate 22.5 mL/min; Detection: 254 nm DAD.

EXAMPLES 39–64

Preparation of N,N-Dimethyl-2-[6-(arylsulfonyl)-6H-thieno[2,3-b]pyrrol-4-yl]ethylamine

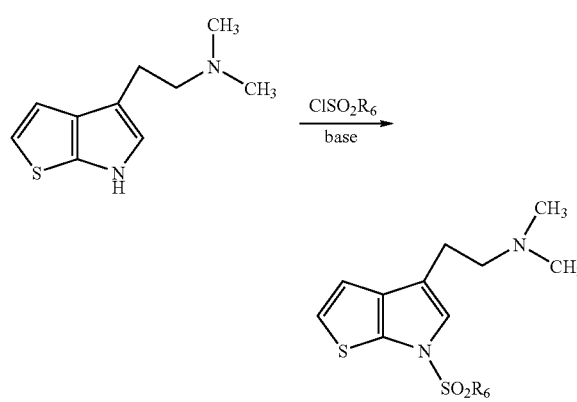

Using essentially the same procedure described in Example 38 hereinabove and employing the appropriate arylsulfonyl chloride, the compounds shown in Table II are obtained and identified by HPLC[2] and mass spectral analyses.

[2]HPLC Conditions: HP 1100 HPLC system; Waters Xterra MS C18, 2 mm (i.d.)×50 mm (length), 3.5 μm column, set at 50° C.; Flow rate 1.0 mL/min; Solvent A: 0.02% formic acid in water; Solvent B 0.02% formic acid in ACN; Gradient: Time 0: 10% B; 2.5 min 90% B; 3 min 90% B; Sample concentration: ~2.0 mM; Injection volume: 5 uL; Detection: 220 nm, 254 nm DAD.

TABLE II

| Ex. No. | R6 | [M + H] | RT (min) |
|---|---|---|---|
| 39 | 3-trifluorophenyl | 403 | 1.71 |
| 40 | 3-chlorophenyl | 370 | 1.69 |
| 41 | 5-chloro-thiophen-2-yl | 376 | 1.71 |
| 42 | 6-chloro-imidazo[2,1-b]thiazol-5-yl | 416 | 1.52 |
| 43 | 2-naphthyl | 386 | 1.82 |
| 44 | 3-methoxyphenyl | 365 | 1.55 |
| 45 | 5-chloro-3-methyl-benzo[b]thiophen-2-yl | 440 | 2 |
| 46 | 2-fluorophenyl | 353 | 1.53 |
| 47 | 3-fluorophenyl | 353 | 1.59 |
| 48 | 2-chlorophenyl | 370 | 1.6 |
| 49 | imidazo[2,1-b]thiazol-5-yl | 382 | 0.67 |
| 50 | 2-Chloro-imidazo[1,2-a]pyridine-3-yl | 410 | 1.44 |
| 51 | 2,6-dichloro-imidazo[2,1-b]thiazol-5-yl | 450 | 1.6 |
| 52 | 4-chlorophenyl | 370 | 1.64 |
| 53 | 2,3-dichlorophenyl | 404 | 1.63 |
| 54 | 3-bromophenyl | 414 | 1.57 |
| 55 | 5-bromo-thiophen-2-yl | 420 | 1.61 |
| 56 | 2-thiophene | 341 | 1.42 |
| 57 | 2,3-dichlorothiophen-5-yl | 410 | 1.73 |
| 58 | 1-naphthylene | 386 | 1.67 |
| 59 | 3-methylphenyl | 349 | 1.63 |
| 60 | 1,2-dimethyl-1H-imidazole-4-yl | 353 | 0.33 |
| 61 | 8-quinoline | 387 | 1.55 |
| 62 | 2-trifluoromethylphenyl | 403 | 1.69 |
| 63 | 4-methoxyphenyl | 365 | 1.54 |
| 64 | 3-chloro-2-methylphenyl | 384 | 1.67 |

EXAMPLES 65–81

Preparation of 2-(4H-Thieno[3,2-b]pyrrol-6-yl]ethylamine Derivatives

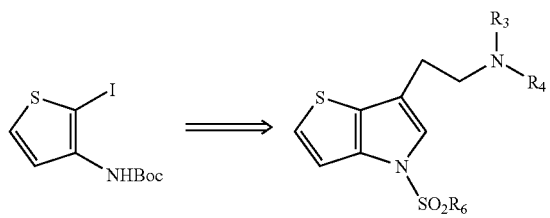

Using essentially the same procedure described in Examples 2–8 and 36–38 hereinabove and employing 2-iodo-3-[(N-t-butoxycarbonyl)amino]thiophene as starting material, and the appropriate ammonium chloride and arylsulfonyl chloride, the compounds shown in Table III are obtained and identified by HPLC[2] and mass spectral analyses.

[2]HPLC Conditions: HP 1100 HPLC system; Waters Xterra MS C18, 2 mm (i.d.)×50 mm (length), 3.5 μm column, set at 50° C.; Flow rate 1.0 mL/min; Solvent A: 0.02% formic acid in water; Solvent B 0.02% formic acid in ACN; Gradient: Time 0: 10% B; 2.5 min 90% B; 3 min 90% B; Sample concentration: ~2.0 mM; Injection volume: 5 uL; Detection: 220 nm, 254 nm DAD.

TABLE III

| Ex. No. | R3 | R4 | R6 | [M + H] | RT (min) |
|---|---|---|---|---|---|
| 65 | H | H | 3-chlorophenyl | 342 | 1.66 |
| 66 | H | H | 2-naphthyl | 357 | 1.77 |
| 67 | H | H | 3-methoxyphenyl | 337 | 1.58 |
| 68 | H | H | 5-chloro-3-methyl-benzo[b]thiophen-2-yl | 412 | 1.97 |
| 69 | H | H | 2-chlorophenyl | 342 | 1.55 |
| 70 | CH3 | CH3 | phenyl | 335 | 1.38 |
| 71 | CH3 | CH3 | 3-trifluorophenyl | 403 | 1.68 |

TABLE III-continued

| Ex. No. | R3 | R4 | R6 | [M + H] | RT (min) |
|---|---|---|---|---|---|
| 72 | CH$_3$ | CH$_3$ | 3-chlorophenyl | 370 | 1.58 |
| 73 | CH$_3$ | CH$_3$ | 5-chloro-thiophen-2-yl | 376 | 1.62 |
| 74 | CH$_3$ | CH$_3$ | 6-chloro-imidazo[2,1-b]-thiazol-5-yl | 416 | 1.42 |
| 75 | CH$_3$ | CH$_3$ | 2-naphthyl | 386 | 1.71 |
| 76 | CH$_3$ | CH$_3$ | 3-methoxyphenyl | 365 | 1.48 |
| 77 | CH$_3$ | CH$_3$ | 5-chloro-3-methyl-benzo[b]thiophen-2-yl | 440 | 1.98 |
| 78 | CH$_3$ | CH$_3$ | 2-fluorophenyl | 353 | 1.4 |
| 79 | CH$_3$ | CH$_3$ | 3-fluorophenyl | 353 | 1.43 |
| 80 | CH$_3$ | CH$_3$ | 2-chlorophenyl | 370 | 1.44 |
| 81 | CH$_3$ | CH$_3$ | imidazo[2,1-b]thiazol-5-yl | 382 | 0.65 |

EXAMPLE 82

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10–25 μl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 μl. To each well is added the following mixture: 80.0 μl of incubation buffer made in 50 mM Tris.HCl buffer (pH 7.4) containing 10.0 mM MgCl$_2$ and 0.5 mM EDTA and 20 μl of [$^3$H]-LSD (S.A., 86.0 Ci/mmol, available from Amersham Life Science), 3.0 nM. The dissociation constant, K$_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 μl of tissue suspension. Nonspecific binding is measured in the presence of 10.0 μM methiothepin. The test compounds are added in 20.0 μl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 μl Microscint®–20 scintillant to each shallow well. The unifilter plate is heat-sealed and counted in a PackardTop-Count® with a tritium efficiency of 31.0%.

Specific binding to the 5-HT6 receptor is defined as the total radioactivity bound less the amount bound in the presence of 10.0 μM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the IC$_{50}$ and the K$_i$ values of test compounds with 95% confidence limits. A linear regression line of data points is plotted, from which the IC$_{50}$ value is determined and the K$_i$ value is determined based upon the following equation:

$$K_i = IC_{50}/(1+L/K_D)$$

where L is the concentration of the radioactive ligand used and K$_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table IV, below.

TABLE IV

| Test Compound (Ex. No.) | 5-HT6 Binding Ki (nM) |
|---|---|
| 8 | 7.5 ± 0.9 |
| 9 | 8.9 ± 0.7 |
| 10 | 4.3 ± 0.5 |
| 11 | 4.9 ± 0.8 |
| 12 | 2.1 ± 0.1 |
| 13 | 16.7 ± 2.4 |
| 14 | 2.3 ± 0.1 |
| 15 | 101.7 ± 5.7 |
| 16 | 12.0 ± 1.2 |
| 17 | 9.3 ± 0.7 |
| 18 | 13.0 ± 1.5 |
| 19 | 3.4 ± 0.6 |
| 20 | 11.3 ± 0.3 |
| 21 | 21.3 ± 1.5 |
| 22 | 13.3 ± 0.7 |
| 23 | 7.1 ± 0.2 |
| 24 | 9.0 ± 0.5 |
| 25 | 17.7 ± 3.2 |
| 26 | 20.0 ± 2.0 |
| 27 | 32.7 ± 4.1 |
| 28 | 9.2 ± 0.8 |
| 29 | 7.8 ± 0.4 |
| 30 | 134.3 ± 10.3 |
| 31 | 8.6 ± 0.8 |
| 32 | 21.0 ± 2.7 |
| 33 | 24.7 ± 1.7 |
| 34 | 13.3 ± 1.5 |
| 35 | 2.4 ± 0.3 |
| 38 | 1.2 ± 0.1 |
| 39 | 2.3 ± 0.5 |
| 40 | 1.6 ± 0.3 |

TABLE IV-continued

| Test Compound | 5-HT6 Binding Ki (nM) |
|---|---|
| 41 | 1.3 ± 0.1 |
| 42 | 0.9 ± 0.1 |
| 43 | 2.5 ± 0.2 |
| 44 | 0.8 ± 0.1 |
| 45 | 20.3 ± 3.4 |
| 46 | 1.8 ± 0.1 |
| 47 | 2.1 ± 0.2 |
| 48 | 5.5 ± 0.5 |
| 49 | 1.1 ± 0.1 |
| 50 | 2.1 ± 0.1 |
| 51 | 6.8 ± 0.6 |
| 52 | 2.6 ± 0.2 |
| 53 | 3.0 ± 0.1 |
| 54 | 1.7 ± 0.1 |
| 55 | 1.1 ± 0.1 |
| 56 | 2.4 ± 0.2 |
| 57 | 4.9 ± 0.3 |
| 58 | 3.6 ± 0.1 |
| 59 | 1.6 ± 0.0 |
| 60 | 50.0 ± 1.0 |
| 61 | 4.7 ± 0.1 |
| 62 | 4.7 ± 0.1 |
| 63 | 3.7 ± 0.1 |
| 64 | 5.9 ± 1.4 |
| 65 | 2.7 ± 0.1 |
| 66 | 9.2 ± 1.0 |
| 67 | 2.0 ± 0.1 |
| 68 | 25.0 ± 1.0 |
| 69 | 2.7 ± 0.2 |
| 70 | 1.2 ± 0.1 |
| 71 | 3.0 ± 0.2 |
| 72 | 1.3 ± 0.1 |
| 73 | 1.6 ± 0.1 |
| 74 | 0.2 ± 0.0 |
| 75 | 3.9 ± 0.2 |
| 76 | 1.3 ± 0.1 |
| 77 | 24.3 ± 1.5 |
| 78 | 2.1 ± 0.1 |
| 79 | 0.9 ± 0.0 |
| 80 | 1.9 ± 0.0 |
| 81 | 0.3 ± 0.0 |
| Comparative Examples | |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the results set forth above, the compounds of the present invention demonstrate significant affinity for the 5-HT6 receptor.

What is claimed is:

1. A compound of formula I

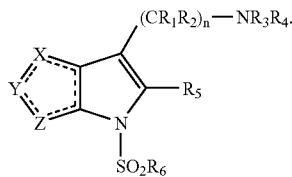

wherein
X is $CR_7$, $SO_m$, or O;
Y is $CR_9$, $SO_m$, or O;
Z is $CR_{10}$, $SO_m$, or O with the proviso that two of X, Y and Z must be $CR_7$, $CR_9$ or $CR_{10}$;

$R_1$ and $R_2$ are each independently H, OH or an optionally substituted $C_1$–$C_6$alkyl group;

$R_3$ and $R_4$ are each independently H or a $C_1$–$C_6$alkyl, $C_2$–$C_6$alkenyl, $C_2$–$C_6$alkynyl, $C_3$–$C_7$cycloalkyl, aryl or group each optionally substituted;

$R_5$ is H, halogen, or a $C_1$–$C_6$alkyl, $C_2$–$C_6$alkoxy, $C_3$–$C_7$cycloalkyl, or aryl group each optionally substituted;

$R_6$ is an optionally substituted heteroaryl group or an optionally substituted 8- to 13-membered bicyclic or tricyclic ring system having a N atom at the bridgehead and optionally containing 1, 2 or 3 additional heteroatoms selected from N, O, or S;

n is an integer of 2, 3, 4 or 5;

$R_7$, $R_9$ and $R_{10}$ are each independently H, halogen, CN, $OCO_2R_{12}$, $CO_2R_{13}$, $CONR_{14}R_{15}$, $SO_pR_{16}$, $NR_{17}R_{18}$, $OR_{19}$, $COR_{20}$, or a $C_1$–$C_6$alkyl, $C_2$–$C_6$alkenyl, $C_2$–$C_6$alkynyl, $C_3$–$C_7$cycloalkyl, or aryl group each optionally substituted;

$R_8$, $R_{11}$, $R_{12}$, $R_{13}$, $R_{16}$, $R_{19}$, and $R_{20}$ are each independently H or a $C_1$–$C_6$alkyl, $C_2$–$C_6$alkenyl, $C_2$–$C_6$alkynyl, $C_3$–$C_6$cycloalkyl, or aryl group each optionally substituted;

$R_{14}$ and $R_{15}$ are each independently H or an optionally substituted $C_1$–$C_6$alkyl group;

$R_{17}$ and $R_{18}$ are each independently H or an optionally substituted $C_1$–$C_4$alkyl group;

$R_{21}$ and $R_{22}$ are each independently H or a $C_1$–$C_6$alkyl, $C_2$–$C_6$alkenyl, $C_2$–$C_6$alkynyl, $C_3$–$C_7$cycloalkyl, or aryl group each optionally substituted; and m, p, q and x are each independently 0 or an integer of 1 or 2; and -------- represents a single bond or a double bond; or a stereoisomer thereof or a pharmaceutically acceptable salt thereof.

2. The compound according to claim 1 wherein X or Z is $SO_m$.

3. The compound according to claim 1 wherein n is 2.

4. The compound according to claim 1 wherein $R_6$ is an optionally substituted heteroaryl group or an optionally substituted 8- to 13-membered bicyclic or tricyclic ring system having a N atom at the bridgehead and optionally containing 1, 2 or 3 additional heteroatoms selected from N, O or S.

5. The compound according to claim 2 wherein m is 0.

6. The compound according to claim 3 wherein $R_3$ and $R_4$ are each independently H or $CH_3$.

7. The compound according to claim 4 wherein $R_6$ is an optionally substituted thienyl or imidazothiazolyl group.

8. The compound according to claim 5 wherein n is 2 and $R_6$ is an optionally substituted thienyl or imidazothiazolyl group.

9. The compound according to claim 1 selected from the group consisting of:

2-{[6-(5-chlorothien-2-yl)sulfonyl]-6H-thieno[2,3-b]pyrrol-4-yl}ethylamine;

2-{[6-(6-chloroimidazo[2,1-b][1,3]thiazol-5-yl)sulfonyl]-6H-thieno[2,3-b]pyrrol-4-yl}-ethylamine;

2-{[6-(5-chloro-3-methylbenzo[b]thien-2-yl)sulfonyl]-6H-thieno[2,3-b]pyrrol-4-yl}-ethylamine;

2-{[6-(imidazo[2,1-b][1,3]thiazol-5-yl)sulfonyl]-6H-thieno[2,3-b]pyrrol-4-yl}ethylamine;

2-{[6-(2-chloroimidazo[1,2-a]pyrid-3-yl)sulfonyl]-6H-thieno[2,3-b]pyrrol-4-yl}-ethylamine;

2-{[6-(2,6-dichloroimidazo[2,1-b][1,3]thiazol-5-yl)sulfonyl]-6H-thieno[2,3-b]pyrrol-4-yl}-ethylamine;
2-{[6-(5-bromothien-2-yl)sulfonyl]-6H-thieno[2,3-b]pyrrol-4-yl}ethylamine;
2-[6-(thien-2-ylsulfonyl)-6H-thieno[2,3-b]pyrrol-4-yl-ethylamine;
2-{[6-(4,5-dichlorothien-2-yl)sulfonyl]-6H-thieno[2,3-b]pyrrol-4-yl}ethylamine;
2-{[6-(1,2-dimethyl-1H-imidazol-4-yl)sulfonyl]-6H-thieno[2,3-b]pyrrol-4-yl}ethylamine;
2-{[6-(quinolin-8-yl)sulfonyl]-6H-thieno[2,3-b]pyrrol-4-yl}-ethylamine;
N,N-dimethyl-2-{[6-(5-chlorothien-2-yl)sulfonyl]-6H-thieno[2,3-b]pyrrol-4-yl]-ethyl}-amine;
N,N-dimethyl-2-{[6-(6-chloroimidazo[2,1-b][1,3]thiazol-5-yl)sulfonyl]-6H-thieno[2,3-b]pyrrol-4-yl}ethylamine;
N,N-dimethyl-2-{[6-(5-chloro-3-methylbenzo[b]thien-2-yl)sulfonyl]-6H-thieno[2,3-b]pyrrol-4-yl}ethylamine;
N,N-dimethyl-2-{[6-(imidazo[2,1-b][1,3]thiazol-5-yl)sulfonyl]-6H-thieno[2,3-b]pyrrol-4-yl}-ethylamine;
N,N-dimethyl-2-{[6-(2-chloroimidazo[1,2-a]pyridin-3-yl)sulfonyl]-6H-thieno[2,3-b]pyrrol-4-yl}ethylamine;
N,N-dimethyl-2-{[6-(2,6-dichloroimidazo[2,1-b]thiazol-5-yl)sulfonyl]-6H-thieno[2,3-b]pyrrol-4-yl}ethylamine;
N,N-dimethyl-2-{[6-(5-bromothien-2-yl)sulfonyl]-6H-thieno[2,3-b]pyrrol-4-ylmethyl}-amine;
N,N-dimethyl-2-{(6-thien-2-ylsulfonyl)-6H-thieno[2,3-b]pyrrol-4-yl]-ethyllamine;
N,N-dimethyl-2-{[6-(4,5-dichlorothien-2-yl)sulfonyl]-6H-thieno[2,3-b]pyrrol-4-yl]-ethyl}-amine;
N,N-dimethyl-2-{[6-(1,2-dimethyl-1H-imidazol-4-yl)sulfonyl]-6H-thieno[2,3-b]pyrrol-4-yl}ethylamine;
N,N-dimethyl-2-{[6-(8-quinolinyl)sulfonyl]-6H-thieno[2,3-b]pyrrol-4-yl}ethylamine;
2-{[4-(5-chloro-3-methyl-benzo[b]thien-2-yl)sulfonyl]-4H-thieno[2,3-b]pyrrol-6-yl}-ethylamine;
N,N-dimethyl-2-{[4-(5-chlorothien-2-yl)sulfonyl]-4H-thieno[2,3-b]pyrrol-6-yl}ethyl-amine;
N,N-dimethyl-2-{[4-(4-chloroimidazo[2,1-b][1,3]thiazol-5-yl)sulfonyl]-4H-thieno[2,3-b]-pyrrol-6-yl}ethylamine;
N,N-dimethyl-2-{[4-(5-chloro-3-methyl-benzo[b]thien-2-yl)sulfonyl]-4H-thieno[2,3-b]pyrrol-6-yl}ethylamine;
N,N-dimethyl-2-{[4-(imidazo[2,1-b][1,3]thiazol-5-yl)sulfonyl]-4H-thieno[2,3-b]pyrrol-6-yl}ethylamine;
N,N-dimethyl-2-{[4-(6-chloroimidazo[2,1-b][1,3]thiazol-5-yl)sulfonyl]-4H-furo[3,2-b]-pyrrol-6-yl}ethylamine;
2-{[1-(6-chloroimidazo[2,1-b]thiazol-5-yl)sulfonyl]-1H-thieno[3,4-b]pyrrol-3-yl}-ethylamine;
N,N-dimethyl-2-{[1-(6-chloroimidazo[2,1-b]thiazol-5-yl)sulfonyl]-1H-thieno[3,4-b]-pyrrol-3-yl}ethylamine;
N,N-dimethyl-2-{[1-(6-chloroimidazo[2,1-b][1,3]thiazol-5-yl)sulfonyl-1H-furo[3,4-b]-pyrrol-3-yl}ethylamine;
2-{[6-(6-chloroimidazo[2,1-b][1,3]thiazol-5-yl)sulfonyl)-6H-furo[2,3-b]pyrrol-4-yl}-ethylamine;
a stereoisomer thereof; and
a pharmaceutically acceptable salt thereof.

10. A pharmaceutical composition which comprises a pharmaceutically acceptable carrier and an effective amount of a compound of formula I

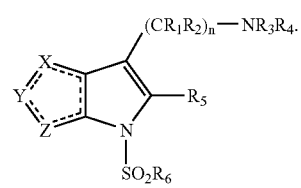

wherein
X is $CR_7$, $SO_m$, or O;
Y is $CR_9$, $SO_m$, or O;
Z is $CR_{10}$, $SO_m$, or O with the proviso that two of X, Y and Z must be $CR_7$, $CR_9$ or $CR_{10}$;
$R_1$ and $R_2$ are each independently H, OH or an optionally substituted $C_1$–$C_6$alkyl group;
$R_3$ and $R_4$ are each independently H or a $C_1$–$C_6$alkyl, $C_2$–$C_6$alkenyl, $C_2$–$C_6$alkynyl, $C_3$–$C_7$cycloalkyl, aryl or group each optionally substituted;
$R_5$ is H, halogen, or a $C_1$–$C_6$alkyl, $C_2$–$C_6$alkoxy, $C_3$–$C_7$cycloalkyl, or aryl group each optionally substituted;
$R_6$ is an optionally substituted heteroaryl group or an optionally substituted 8- to 13-membered bicyclic or tricyclic ring system having a N atom at the bridgehead and optionally containing 1, 2 or 3 additional heteroatoms selected from N, O, or S
n is an integer of 2, 3, 4 or 5;
$R_7$, $R_9$ and $R_{10}$ are each independently H, halogen, CN, $OCO_2R_{12}$, $CO_2R_{13}$, $CONR_{14}R_{15}$, $SO_pR_{16}$, $NR_{17}R_{18}$, $OR_{19}$, $COR_{20}$, or a $C_1$–$C_6$alkyl, $C_2$–$C_6$alkenyl, $C_2$–$C_6$alkynyl, $C_3$–$C_7$cycloalkyl, or aryl group each optionally substituted;
$R_8$, $R_{11}$, $R_{12}$, $R_{13}$, $R_{16}$, $R_{19}$, and $R_{20}$ are each independently H or a $C_1$–$C_6$alkyl, $C_2$–$C_6$alkenyl, $C_2$–$C_6$alkynyl, $C_3$–$C_6$cycloalkyl, or aryl group each optionally substituted;
$R_{14}$ and $R_{15}$ are each independently H or an optionally substituted $C_1$–$C_6$alkyl group
$R_{17}$ and $R_{18}$ are each independently H or an optionally substituted $C_1$–$C_4$alkyl group
$R_{21}$ and $R_{22}$ are each independently H or a $C_1$–$C_6$alkyl, $C_2$–$C_6$alkenyl, $C_2$–$C_6$alkynyl, $C_3$–$C_7$cycloalkyl, or aryl group each optionally substituted; and
m, p, q and x are each independently 0 or an integer of 1 or 2; and
------- represents a single bond or a double bond; or
a stereoisomer thereof or a pharmaceutically acceptable salt thereof.

11. The composition according to claim 10 having a formula I compound wherein X or Z is $SO_m$.

12. The composition according to claim 11 having a formula I compound wherein n is 2 and m is 0.

13. The composition according to claim 12 having a formula I compound wherein $R_6$ is an optionally substituted thienyl or imidazothiazolyl group and $R_4$ and $R_5$ are each independently H or $CH_3$.

14. The composition according to claim 10 having a formula I compound selected from the group consisting of:
2-{[6-(5-chlorothien-2-yl)sulfonyl]-6H-thieno[2,3-b]pyrrol-4-yl}ethylamine;
2-{[6-(6-chloroimidazo[2,1-b][1,3]thiazol-5-yl)sulfonyl]-6H-thieno[2,3-b]pyrrol-4-yl}-ethylamine;
2-{[6-(5-chloro-3-methylbenzo[b]thien-2-yl)sulfonyl]-6H-thieno[2,3-b]pyrrol-4-yl}-ethylamine;

2-{[6-(imidazo[2,1-b][1,3]thiazol-5-yl)sulfonyl]-6H-thieno[2,3-b]pyrrol-4-yl}ethylamine;
2-{[6-(2-chloroimidazo[1,2-a]pyrid-3-yl)sulfonyl]-6H-thieno[2,3-b]pyrrol-4-yl}-ethylamine;
2-{[6-(2,6-dichloroimidazo[2,1-b][1,3]thiazol-5-yl)sulfonyl]-6H-thieno[2,3-b]pyrrol-4-yl}-ethylamine;
2-{[6-(5-bromothien-2-yl)sulfonyl]-6H-thieno[2,3-b]pyrrol-4-yl}ethylamine;
2-[6-(thien-2-ylsulfonyl)-6H-thieno[2,3-b]pyrrol-4-yl-ethylamine;
2-{[6-(4,5-dichlorothien-2-yl)sulfonyl]-6H-thieno[2,3-b]pyrrol-4-yl}ethylamine;
2-{[6-(1,2-dimethyl-1H-imidazol-4-yl)sulfonyl]-6H-thieno[2,3-b]pyrrol-4-yl}ethylamine;
2-{[6-(quinolin-8-yl)sulfonyl]-6H-thieno[2,3-b]pyrrol-4-yl}-ethylamine;
N,N-dimethyl-2-{[6-(5-chlorothien-2-yl)sulfonyl]-6H-thieno[2,3-b]pyrrol-4-yl]-ethyl}-amine;
N,N-dimethyl-2-{[6-(6-chloroimidazo[2,1-b][1,3]thiazol-5-yl)sulfonyl]-6H-thieno[2,3-b]pyrrol-4-yl}ethylamine;
N,N-dimethyl-2-[6-(5-chloro-3-methylbenzo[b]thien-2-yl)sulfonyl]-6H-thieno[2,3-b]pyrrol-4-yl}ethylamine;
N,N-dimethyl-2-{[6-(imidazo[2,1-b][1,3]thiazol-5-yl)sulfonyl]-6H-thieno[2,3-b]pyrrol-4-yl}-ethylamine;
N,N-dimethyl-2-{[6-(2-chloroimidazo[1,2-a]pyridin-3-yl)sulfonyl]-6H-thieno[2,3-b]pyrrol-4-yl}ethylamine;
N,N-dimethyl-2-{[6-(2,6-dichloroimidazo[2,1-b]thiazol-5-yl)sulfonyl]-6H-thieno[2,3-b]pyrrol-4-yl}ethylamine;
N,N-dimethyl-2-{[6-(5-bromothien-2-yl)sulfonyl]-6H-thieno[2,3-b]pyrrol-4-yl}amine;
N,N-dimethyl-2-{[(6-thien-2-ylsulfonyl)-6H-thieno[2,3-b]pyrrol-4-yl]-ethyllamine;
N,N-dimethyl-2-{[6-(4,5-dichlorothien-2-yl)sulfonyl]-6H-thieno[2,3-b]pyrrol-4-yl]-ethyl}-amine;
N,N-dimethyl-2-{[6-(1,2-dimethyl-1H-imidazol-4-yl)sulfonyl]-6H-thieno[2,3-b]pyrrol-4-yl}ethylamine;
N,N-dimethyl-2-{[6-(8-quinolinyl)sulfonyl]-6H-thieno[2,3-b]pyrrol-4-yl}ethylamine;
2-{[4-(5-chloro-3-methyl-benzo[b]thien-2-yl)sulfonyl]-4H-thieno[2,3-b]pyrrol-6-yl}-ethylamine;
N,N-dimethyl-2-{[4-(5-chlorothien-2-yl)sulfonyl]-4H-thieno[2,3-b]pyrrol-6-yl}ethyl-amine;
N,N-dimethyl-2-[4-(4-chloroimidazo[2,1-b][1,3]thiazol-5-yl)sulfonyl]-4H-thieno[2,3-b]-pyrrol-6-yl}ethylamine;
N,N-dimethyl-2-{[4-(5-chloro-3-methyl-benzo[b]thien-2-yl)sulfonyl]-4H-thieno[2,3-b]pyrrol-6-yl}ethylamine;
N,N-dimethyl-2-{[4-(imidazo[2,1-b][1,3]thiazol-5-yl)sulfonyl]-4H-thieno[2,3-b]pyrrol-6-yl}ethylamine;
N,N-dimethyl-2-{[4-(6-chloroimidazo[2,1-b][1,3]thiazol-5-yl)sulfonyl]-4H-furo[3,2-b]-pyrrol-6-yl}ethylamine;
2-{[1-(6-chloroimidazo[2,1-b]thiazol-5-yl)sulfonyl]-1H-thieno[3,4-b]pyrrol-3-yl}-ethylamine;
N,N-dimethyl-2-{[1-(6-chloroimidazo[2,1-b]thiazol-5-yl)sulfonyl]-1H-thieno[3,4-b]-pyrrol-3-yl}ethylamine;
N,N-dimethyl-2-{[1-(6-chloroimidazo[2,1-b][1,3]thiazol-5-yl)sulfonyl]-1H-furo[3,4-b]-pyrrol-3-yl}ethylamine;
2-{[6-(6-chloroimidazo[2,1-b][1,3]thiazol-5-yl)sulfonyl]-6H-furo[2,3-b]pyrrol-4-yl}-ethylamine;
a stereoisomer thereof; and
a pharmaceutically acceptable salt thereof.

15. A process for the preparation of a compound of formula I

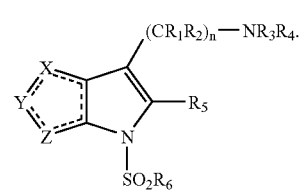

wherein
X is $CR_7$, $SO_m$, or O;
Y is $CR_9$, $SO_m$, or O;
Z is $CR_{10}$, $SO_m$, or O with the proviso that two of X, Y and Z must be $CR_7$, $CR_9$ or $CR_{10}$;
$R_1$ and $R_2$ are each independently H, OH or an optionally substituted $C_1$–$C_6$alkyl group;
$R_3$ and $R_4$ are each independently H or a $C_1$–$C_6$alkyl, $C_2$–$C_6$alkenyl, $C_2$–$C_6$alkynyl, $C_3$–$C_7$cycloalkyl, aryl or group each optionally substituted;
$R_5$ is H, halogen, or a $C_1$–$C_6$alkyl, $C_2$–$C_6$alkoxy, $C_3$–$C_7$cycloalkyl, or aryl group each optionally substituted;
$R_6$ is an optionally substituted heteroaryl group or an optionally substituted 8- to 13-membered bicyclic or tricyclic ring system having a N atom at the bridgehead and optionally containing 1, 2 or 3 additional heteroatoms selected from N, O, or S
n is an integer of 2, 3, 4 or 5;
$R_7$, $R_9$ and $R_{10}$ are each independently H, halogen, CN, $OCO_2R_{12}$, $CO_2R_{13}$, $CONR_{14}R_{15}$, $SO_pR_{16}$, $NR_{17}R_{18}$, $OR_{19}$, $COR_{20}$, or a $C_1$–$C_6$alkyl, $C_2$–$C_6$alkenyl, $C_2$–$C_6$alkynyl, $C_3$–$C_7$cycloalkyl, or aryl group each optionally substituted;
$R_8$, $R_{11}$, $R_{12}$, $R_{13}$, $R_{16}$, $R_{19}$, and $R_{20}$ are each independently H or a $C_1$–$C_6$alkyl, $C_2$–$C_6$alkenyl, $C_2$–$C_6$alkynyl, $C_3$–$C_6$cycloalkyl, or aryl group each optionally substituted;
$R_{14}$ and $R_{15}$ are each independently H or an optionally substituted $C_1$–$C_6$alkyl group
$R_{17}$ and $R_{18}$ are each independently H or an optionally substituted $C_1$–$C_4$alkyl group
$R_{21}$ and $R_{22}$ are each independently H or a $C_1$–$C_6$alkyl, $C_2$–$C_6$alkenyl, $C_2$–$C_6$alkynyl, $C_3$–$C_7$cycloalkyl, or aryl group each optionally substituted; and
m, p, q and x are each independently 0 or an integer of 1 or 2; and
-------- represents a single bond or a double bond
which process comprises reacting a compound of formula II

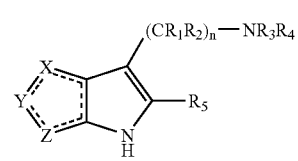

wherein X, Y Z, n, $R_1$, $R_2$, $R_3$, $R_4$ and $R_5$ are as described hereinabove with a sulfonyl chloride, $ClSO_2R_6$, in the presence of a base optionally in the presence of a solvent.

* * * * *